(12) United States Patent
Stehlik et al.

(10) Patent No.: US 6,278,896 B1
(45) Date of Patent: Aug. 21, 2001

(54) BIOCOMPATIBLE GLASS-METAL THROUGH-DUCTS AND THEIR USE

(75) Inventors: Vojtech Stehlik, Landshut; Oswald Puscher, Gammelsdorf, both of (DE)

(73) Assignee: Schott Glas, Mainz (DE)

( * ) Notice: Subject to any disclaimer, the term of this patent is extended or adjusted under 35 U.S.C. 154(b) by 0 days.

(21) Appl. No.: 09/399,142

(22) Filed: Sep. 20, 1999

(30) Foreign Application Priority Data

Sep. 18, 1998 (DE) .............................................. 198 42 943

(51) Int. Cl.⁷ ...................................................... A61N 1/18
(52) U.S. Cl. ......................... 607/35; 607/9; 174/152 GM
(58) Field of Search ................................... 174/152 GM; 607/9, 36

(56) References Cited

U.S. PATENT DOCUMENTS

| 3,770,568 | 11/1973 | Graff et al. . |
|---|---|---|
| 4,220,813 | 9/1980 | Kyle . |
| 4,430,376 | 2/1984 | Box . |
| 4,566,892 | 1/1986 | Ertel . |
| 4,915,719 | 4/1990 | Saffari . |
| 5,633,531 | 5/1997 | Hornig et al. . |
| 5,709,724 | 1/1998 | Naugler et al. . |

FOREIGN PATENT DOCUMENTS

| 21 08 425 | 9/1972 | (DE) . |
|---|---|---|
| 40 14 264 | 5/1990 | (DE) . |
| 0137488 | 4/1985 | (EP) . |
| 952660 | 10/1961 | (GB) . |

*Primary Examiner*—Mark Bockelman
(74) *Attorney, Agent, or Firm*—Millen, White, Zelano & Branigan, P.C.

(57) ABSTRACT

Biocompatible glass-metal through-ducts comprised of an outside conductor, a biocompatible glass and at least one inside conductor, with the outside conductor comprising a nickel-free, stainless, chemically resistant steel (high-grade steel), is used in implantable medical hardware and devices.

10 Claims, 1 Drawing Sheet

BIOCOMPATIBLE GLASS-METAL THROUGH-DUCTS AND THEIR USE

Figure 1:
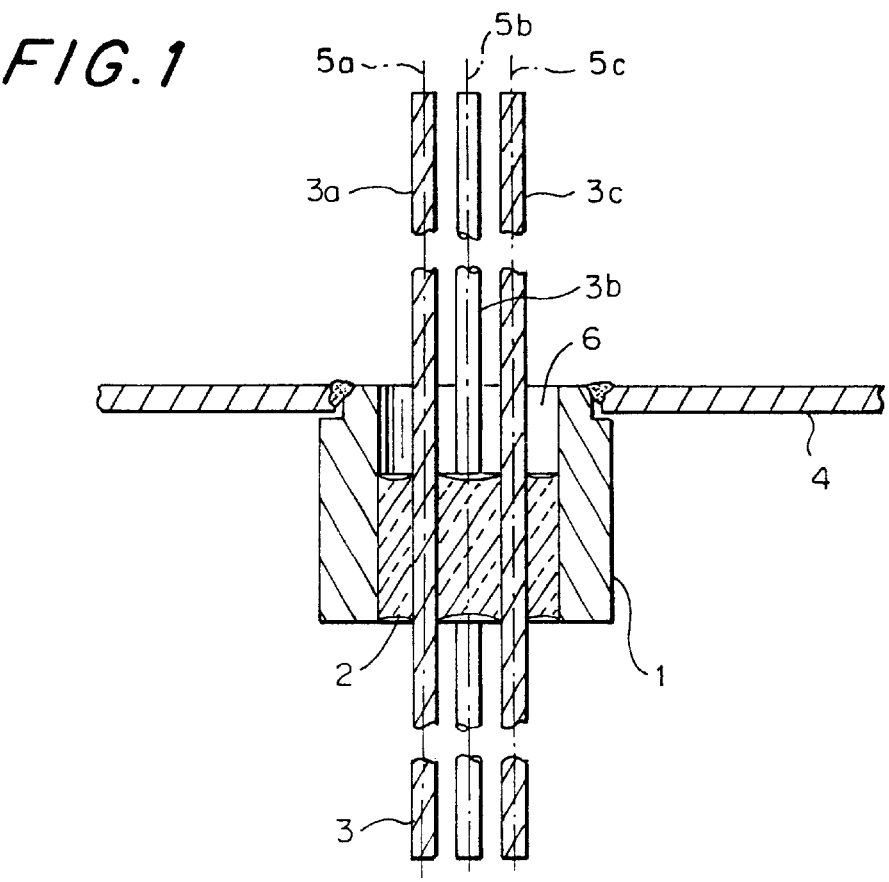

The invention relates to biocompatible glass-metal through-ducts and their use in implantable medical hardware and devices as well as the hardware and devices themselves.

Glass-metal through-ducts are of great importance in the most varied applications, thus, e.g., in electrical engineering. Here, in particular the long-term thermeticity of the through-ducts of electrical conductors in housings for components of electronics, especially also of optoelectronics and motor vehicle electronics and sensor technology, is required, which makes it necessary to have melt connections between the glasses and various metals.

Implantable, biocompatible through-ducts represent a characteristic in glass-metal through-ducts in hermetically scaled components. They are used in implantable medical devices, e.g., pacemakers. Biocompatibility, high resistance to corrosion and good long-term resistance of all of the components used are essential for these through-ducts.

Implantable, biocompatible through-ducts that consist of an outside conductor that is made of titanium, a biocompatible glass and an inside conductor that is made of tantalum are known.

Based on its long-term resistance, its good processibility and based on the possibility of varying its thermal expansion coefficient with the composition in a certain range and thus making possible an adapted or a so-called pressure-glass through-duct with a sealed melt connection to the respective metal, glass is very well suited as a material for hermetic through-ducts. Of course, special requirements with respect to biocompatibility, i.e., ultimately with respect to composition, are set for a glass that is to be implanted. Glasses that have no toxic components or only small amounts that are physiologically harmless are described in, e.g., Patent DE 40 15 264 C1, incorporated herein in its entirety by reference. They are also used as capsule material for implantable minisenders or transponders.

Based on its chemical resistance and its biocompatiblity, tantalum is known as a suitable material for inside conductors.

For many implantable medical devices, titanium is used also as an outside conductor in the above-mentioned glass-metal through-ducts. This metal has a very good corrosion resistance and high biocompatibility.

The biocompatible glass-metal through-ducts that are produced at this time are very expensive, however, especially because of the use of titanium in their production. For the purpose of ensuring extensive medical supply, to which now obvious implants of, for example, pacemakers also always belong because of the high level of know-how in medicine and medical technology, it is important to supply implants or their components on an economical basis.

It is the object of the invention to find biocompatible, implantable, hermetic glass-metal through-ducts that can be produced economically especially because of their production processes and the materials that are used.

This object is achieved by the glass-metal through-ducts that are described in claim 1.

They are built up from an outside conductor made of nickel free, stainless chemically insert high grade steel, a biocompatible glass and at least one inside conductor.

The outside conductor comprises a nickel-free, stainless, chemically resistant steel (high-grade steel). It has namely been found, surprisingly enough, that such steels are both sufficiently corrosion-resistant and biocompatible and are suitable based on their additional material properties such as good machinability and good weldability to replace the previously used, expensive titanium conductor. Nickel-free is defined here as a content of at most 0.3% Ni, which also meets the medically indicated requirements for the absence of nickel. Within the context of the medical acceptance process, additional medically indicated requirements for the extensive test are reviewed. The respective requirements can be subjected to transformations because of expanding knowledge and improved methods of analysis. Such high-grade steels are known in the art. As examples, a high-grade austenitic steel (a) and a high-grade ferritic steel (b) can be mentioned here:

a) Stainless steel that consists of 0–0.1% C; 16.0–20.0% Cr; 16.0–20.0% Mn; 1.8–2.5% Mo; 0.7–1.0% N; 0–0.3% Ni, 0–0.05% P; 0–0.05% S; 0–1.0% Si; 0–0.2% V, the remainder including the smelting-induced contaminant iron.

b) Stainless steel that consists of 0–0.03% C; 17.5–18.5% Cr; 0–0.5% Mn; 2.0–2.5% Mo; 0–0.3% Ni; 0–0.03% P; 0.15–0.35% S; 0–1.0% Si; 0.3–1.0% Ti; the remainder including the smelting-induced contaminant iron.

The use of such standard, reasonably priced high-grade steels in the through-ducts according to the invention provides for an enormous price reduction in their production.

As a sealing element and an electric insulator for vitrification, any biocompatible glasses can be used. Such glasses are tissue-compatible, do not cause any rejection reaction in the body and are sufficiently corrosion-resistant.

As examples, the glasses of the following ranges of composition (in % by weight based on oxide) can be mentioned:

40–45 $SiO_2$; 1–4 $B_2O_3$; 35–40 $Al_2O_3$; 0–2 BaO; 4–10 CaO; 4–10 MgO; 4–10 $P_2O_5$; 0–1 $MnO_2$

65–70 $SiO_2$; 0–1 $B_2O_3$; 3–5 $Al_2O_3$; 11–15 $Na_2O$; 2–4 $K_2O$; 0–2 BaO; 4–6 CaO; 2–5 $Fe_2O_3$; 2–4 MgO

64–70 $SiO_2$; 15–22 $B_2O_3$; 0–3 $Al_2O_3$; 0–1 $Li_2O$; 0–1 $Na_2O$; 5–11 $K_2O$; 0–1 ZnO.

Tantalum can be used as an inside conductor. The use of other materials with a thermal expansion coefficient $\alpha_{200/400}$ of between $40\times10^{-7}$ and $110\times10^{-7}$ $K^{-1}$ that are suitable for scaling is also possible. Here, e.g., nickel-free, stainless, high-grade ferritic steels can be mentioned, for example AISI 446 (US standard) or similar high-grade ferritic steels. Inside conductors that are made of high-grade steel are known to date only in the general industrial area, for example in refrigerator understructures. Platinum and platinum alloys are also well suited because of their biocompatiblity and their good solderability. Here in particular Pt/Ir alloys can be mentioned. In these alloys, the iridium proportion is in most cases 5–30%.

The electric through-ducts according to the invention are extremely well suited for use in implants, such as, e.g., pacemakers and other devices for functional electrosimulation, for example auditory implants, cerebral pacemakers, defibrillators and in dynamic myoplasty, respiratory pacemakers, leg and hand pacemakers. Their use is not limited to this field of use, however; they can be used just as well in, for example, industrial sensor technology or similar fields.

The structure of the glass-metal through-ducts according to the invention is explained in more detail below based on the drawing. As an example, FIG. 1 shows a section in diagrammatic visualization by an embodiment of the invention. The material combination according to the invention is not limited to this embodiment, of course, but rather is suitable for all forms of glass-metal through-ducts that are known to one skilled in the art, thus, also, for example, for those that contain a multilayer chip as a condenser (EMV filter).

Figure 2:
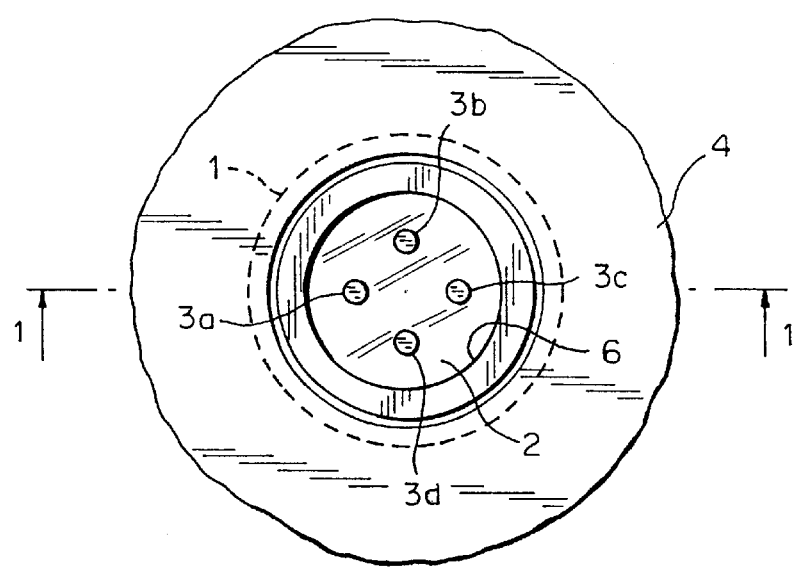

FIGS. 1 and 2 show a glass-metal through-duct, whose outside conductor 1 is designed ring-shaped and that consists of a nickel-free, stainless, chemically resistant steel (high-grade steel) of the above-mentioned composition b) (high-grade ferritic steel Sandvik 1802 by the Sandvik Steel Company). Four-pole inside conductor 3 comprising wires 3a, 3b, 3c, and 3d are centered in an outside conductor. The electroconductive wires 3a–3d occupy excellent positions on a four-figure axis of rotation. Their individual axes 5a–5d are also drawn in. The wires consist of tantalum, but they can also consist of, for example, platinum or platinum/iridium alloys. Inside conductor 3 is sealed in an insulating glass element 2, which fills about ⅔ of the space 6 inside the outside conductor 1 (of course, complete vitrification would also be possible) and is also fused with the latter. The glass is a biocompatible glass from the composition area that is mentioned above as the second. A metal housing 4 of the device, in which the through-duct is used, is already welded to outside conductor 1.

The biocompatible glass-metal through-ducts according to the invention correspond in terms of all requirements that are set for such through-ducts to the through-ducts that have been used to date for implants and are distinguished in that they can be produced more economically than the previously known through-ducts based on the high-grade steels that are used as outside conductor materials.

What is claimed is:

1. A biocompatible glass-metal through-duct having an outside conductor, a biocompatible glass and at least one inside conductor, wherein the outside conductor is comprised of a stainless, chemically resistant steel having a nickel content in the range of 0-0.3%.

2. A glass-metal through-duct according to claim 1, wherein the at least one inside conductor is comprised of tantalum.

3. An implantable medical device or medical hardware with at least one glass-metal through-duct according to claim 2.

4. A glass-metal through-duct according to claim 1, wherein the at least one inside conductor is comprised of platinum or platinum alloys.

5. An implantable medical device or medical hardware with at least one glass-metal through-duct according to claim 3.

6. A glass-metal through-duct according to claim 1, wherein the at least one inside conductor is comprised of a nickel-free, stainless, high-grade ferritic steel.

7. An implantable medical device or medical hardware with at least one glass-metal through-duct according to claim 4.

8. An implantable medical device or medical hardware with at least one glass-metal through-duct according to claim 1.

9. The glass to metal through-duct of claim 1, wherein there are a plurality of inside conductors.

10. The glass to metal through-duct of claim 1, wherein there are four inside conductors.

* * * * *